US00PP36401P2

(12) United States Plant Patent
Bennett

(10) Patent No.: US PP36,401 P2
(45) Date of Patent: Jan. 21, 2025

(54) ***ROSA HYBRIDA* SHRUB PLANT NAMED 'AUSB18A15'**

(50) Latin Name: *Rosa hybrida*
Varietal Denomination: AUSB18A15

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 18/445,813

(22) Filed: Feb. 14, 2024

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

(56) References Cited

PUBLICATIONS

CPVO Register. 2024. citation for 'AUSB18A15'. https://online.plantvarieties.eu/publicSearch?denomination=ausb18a15. 2 pages (Year: 2024).*

* cited by examiner

*Primary Examiner* — Karen M Redden
(74) *Attorney, Agent, or Firm* — KPPB LLP

(57) ABSTRACT

A variety of rose plant of the shrub class, named 'AUSB18A15'. The 'AUSB18A15' is a variety of a rose with sprays of cupped, mid-pink blooms with a medium strong Old Rose/fruity fragrance capable of repeat flowering.

1 Drawing Sheet

Classification: The present invention relates to a new *Rosa hybrida* shrub of the market class 'English Rose'.

Variety denomination: The new plant has the varietal denomination 'AUSB18A15'.

ORIGIN OF INVENTION

This invention relates to a new and distinct variety of shrub rose plant named 'AUSB18A15', which was originated from the cross-pollination of the two 'unnamed' and unpatented seedlings of *Rosa hybrida.*

BACKGROUND OF THE INVENTION

The primary objective of this breeding was to produce a rose with sprays of cupped mid-pink blooms, and medium-sized, bushy shrub with a medium-strong Old Rose/fruity fragrance.

SUMMARY OF THE INVENTION

Among the features which distinguish the new variety from others presently available and commercial rose cultivars known to the inventor is the following combination of characteristics: sprays of cupped, mid-pink blooms with a medium strong Old Rose/fruity fragrance in a medium-sized, bushy shrub capable of repeat flowering.

Asexual reproduction of the new variety by budding as performed in Albrighton, United Kingdom shows that the foregoing and other distinguishing characteristics come true to form and are established and transmitted through succeeding asexual propagations. 'AUSB18A15' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSB18A15' are two unnamed seedlings. The new rose may be distinguished from its seed parent, by the following combination of characteristics: the seed parent is paler in color and has a climbing growth habit when compared to 'AUSB18A15'. The new rose may be distinguished from its pollen parent, by the following combination of characteristics: the pollen parent has very few petals and a climbing growth habit when compared to 'AUSB18A15', which is a shrub rose.

COMPARISON WITH THE CLOSEST COMMERCIALLY AVAILABLE CULTIVAR

The most similar rose variety is 'AUSmerchant' (U.S. Plant Pat. No. 19,828). Both blooms are similar in color, however, 'AUSmerchant' has more petals (approx. 130) when compared to 'AUSB18A15' (approx. 100). 'AUSB18A15' also has a different fragrance of Old Rose/fruit, when compared to 'AUSmerchant' which has a strong Tea fragrance. There is also a difference in the growth habit, with 'AUSB18A15' having a semi-upright growth habit, whereas 'AUSmerchant' is moderately spreading in its growth. Finally, the leaf glossiness of the upper side is stronger on 'AUSB18A15' when compared to 'AUSmerchant'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSB18A15' specimens were made at a garden in Albrighton, Wolverhampton, United Kingdom. The following description is of 7-year-old rose plants of the new variety grown in a garden environment in Albrighton, United Kingdom in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.6 cm long and 2.3 cm in diameter when the petals start to unfurl.

*Form*.—The bud form is short pointed ovoid globular.

*Color*.—When sepals first divide, the bud color is RHS 51A (red group). When half blown, the upper sides of the petals are RHS 55B (red group) and the lower sides of the petals are RHS 62A (red-purple group).

*Calyx*.—Shape: star shape, with the sepals folding back against the stems. Length: 6.1 cm. Diameter: 6.1 cm.

*Sepals*.—Arrangement: Regular. Color: Upper Surface: RHS 147C (yellow-green group) often with irregular flashes of approximately RHS 59B (red-purple group). Lower Surface: RHS 146C (yellow-green group) often with flashes of approximately RHS 59B (red-purple group). Length: 2.5 cm. Width: 1 cm. Shape: Lanceolate. Apex: Overall shape, lanceolate. Margin: Smooth/glandular. Surface texture: Upper Surface: Smooth, slightly hairy. Lower Surface: Smooth. Number: There are 2 to 3 lightly appendaged sepals, and 2 to 3 unappendaged sepals with smooth glandular edges.

*Receptacles*.—Color: RHS 143B (green group). Shape: Funnel. Size: Medium, about 1.1 cm long×1.2 cm wide. Surface: Smooth.

*Peduncle*.—Length: Medium/Short, averaging about 5 cm. Surface: Smooth. Color: RHS 184A (grayed-purple group). Strength: Normal.

Blooms:

*Type*.—Cupped.

*Size*.—Large, average open diameter is about 9 cm and average depth is about 3.1 cm.

*Borne*.—Several together in clusters of 4-14 with blooms having a flat shape.

*Penduncle*.—Strength: Normal, average length is about 5 cm. Diameter: 0.2 cm.

*Form*.—When first open, bloom is globular. Permanence of bloom flattens: outer petals curl back.

*Upper profile*.—Flat.

*Lower profile*.—Flattened convex.

Petalage: Number of petals under normal conditions: 100.

*Color*.—The upper sides of the petals are RHS 56A (red group) at the base to RHS 55B (red group) at the top. The reverse sides of the petals are RHS 55B (red group). The base of the petals has a small/medium basal spot of RHS 3A (yellow group).

*Variegations*.—None.

*Discoloration*.—The general tonality at the end of the first day is RHS N57A (red-purple group), and at the end of the third day is RHS 55B (red group).

*Fragrance*.—Moderate strong. Character of fragrance: Old Rose/fruit.

Petals:

*Texture*.—Smooth, satiny and thin on both sides.

*Size*.—Width: 3.7 cm. Length: 3.9 cm.

*Surface*.—Smooth.

*Shape*.—Obovate.

*Margin*.—Mostly entire.

*Apex shape*.—Rounded with notches.

*Base shape*.—Acute.

*Form*.—Edges slightly quilled.

*Arrangement*.—Quartered.

*Petaloids*.—Number: 7. Color: RHS 55B (red group). Length: 1.5 cm. Width: 0.8 cm. Shape: Obovate. Margin: Irregular.

*Persistence*.—Petals drop off cleanly before drying.

*Lastingness*.—On the plant: short about 3-5 days. As a cut flower: not tested.

Reproductive parts:

*Stamens*.—Number: approximately 70-80. Length: approximately 1 cm.

*Anthers*.—Length: approximately 0.25 cm. Color: RHS 23C (yellow-orange group). Arrangement: Regular around styles mixed with petaloids.

*Filaments*.—Color: RHS 8A (yellow group) and RHS 61B (red-purple group). Length: 0.8 cm.

*Pollen*.—Color: RHS 12A (yellow group). Amount: Scarce.

*Pistils*.—Number: approximately 50-55. Length: approximately 1 cm.

*Styles*.—Color: RHS 155A (grayed-white group). Length: 0.9 cm.

*Stigmas*.—Color: RHS 154C (yellow-green group). Length: approximately 0.1 cm.

*Hips*.—NONE Observed.

PLANT CHARACTERISTICS

Plant form: Shrub.

Plant growth: Medium and branching.

Age to maturity: 2 years.

Mature plant: Height: 110 cm. Width: 125 cm.

Rootstock: *Rosa dumetorum* 'Laxa' (not patented) for the observed plants in the United Kingdom. 'Dr Huey' (not patented) in the USA.

Foliage:

*Number*.—Leaflets on normal mid-stem leaves is: 5 (including terminal leaflet).

*Size*.—Medium, about 17 cm long×13 cm wide.

*Quantity*.—Normal. Number of leaves per flowering stem is: approximately 6-10.

*Color*.—New foliage: Upper side: RHS 175B (grayed-orange group) with central flash of 144A (yellow-green group). Lower side: RHS 176A (grayed-orange group). Old foliage: Upper side: RHS 147A (yellow-green group). Lower side: RHS 146B (yellow-green group).

*Glossiness*.—Strong.

Leaflets:

*Size*.—About 6.7 cm long×4 cm wide.

*Shape*.—Pointed oval.

*Base shape*.—Rounded.

*Apex shape*.—Acuminate.

*Texture*.—Upper side: Leathery. Lower side: Leathery.

*Edge*.—Serrated.

*Serrations*.—Single/Large.

*Petiole*.—Color: upper side is RHS 185B (grayed-purple group), matures to RHS 138A (green group) on older leaves. Length: 5.1 cm. Width: 0.2 cm. Surface Texture: Smooth with occasional prickle on underside.

*Petiole rachis*.—Color: upper side RHS 152A (yellow-green group) typically, with some RHS 185B (grayed-purple group). Underside: smooth with prickles. Lower Surface: smooth.

*Stipules*.—Length: 2.6 cm. Shape: Lateral. Descriptor: smooth/glandular. Apex: Acute. Color: RHS 144A (yellow-green group).

*Auricle*.—Shape: Lanceolate. Length: 0.6 cm. Width: 0.2 cm. Color: RHS 144A (yellow-green group).

*Vein color*.—RHS 147A (yellow-green group).

*Venation pattern*.—Reticulate.

Wood:

*New wood*.—Color: RHS 175A (grayed-orange group). Bark: Smooth.

*Old wood*.—Color: RHS 143A (green group) to 143B (green group). Bark: Smooth.

Branching habit:

*Number*.—2-4 per main stem.

*Dimensions*.—Length: 80-100 cm. Diameter: 0.8-0.9 cm.

Stems:

*Mature stem*.—Length: approximately 120 cm. Diameter: 1.1 cm.

*Internode distance*.—Approximately 8.5 cm. The above measurements are all variable, depending on growing conditions in a season.

*Stem pubescence present*.—No.

Prickles:

*Quantity*.—On main canes from base: ordinary/few. Number per stem length: 6-8 per 20 cm. On laterals from main canes: ordinary/few. Number per stem length: 6-8 per 20 cm.

*Form*.—Slightly hooked downward/deep concave.

*Length*.—0.7 cm.

*Color when young*.—RHS 61A (red-purple group).

*Color when mature*.—RHS 59A (red-purple group).

Small prickles:

*Quantity*.—Main stalk: Few. Number per stem length: 5 per 20 cm. Laterals: Few. Number per stem length: 5 per 20 cm.

*Color*.—When young: RHS 61A (red-purple group). When mature: RHS 59A (red-purple group).

Disease resistance:

*Powdery mildew* (*podosphaera pannosa*).—Resistant.

*Downy mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class, named 'AUSB18A15', substantially as herein shown and described.

* * * * *

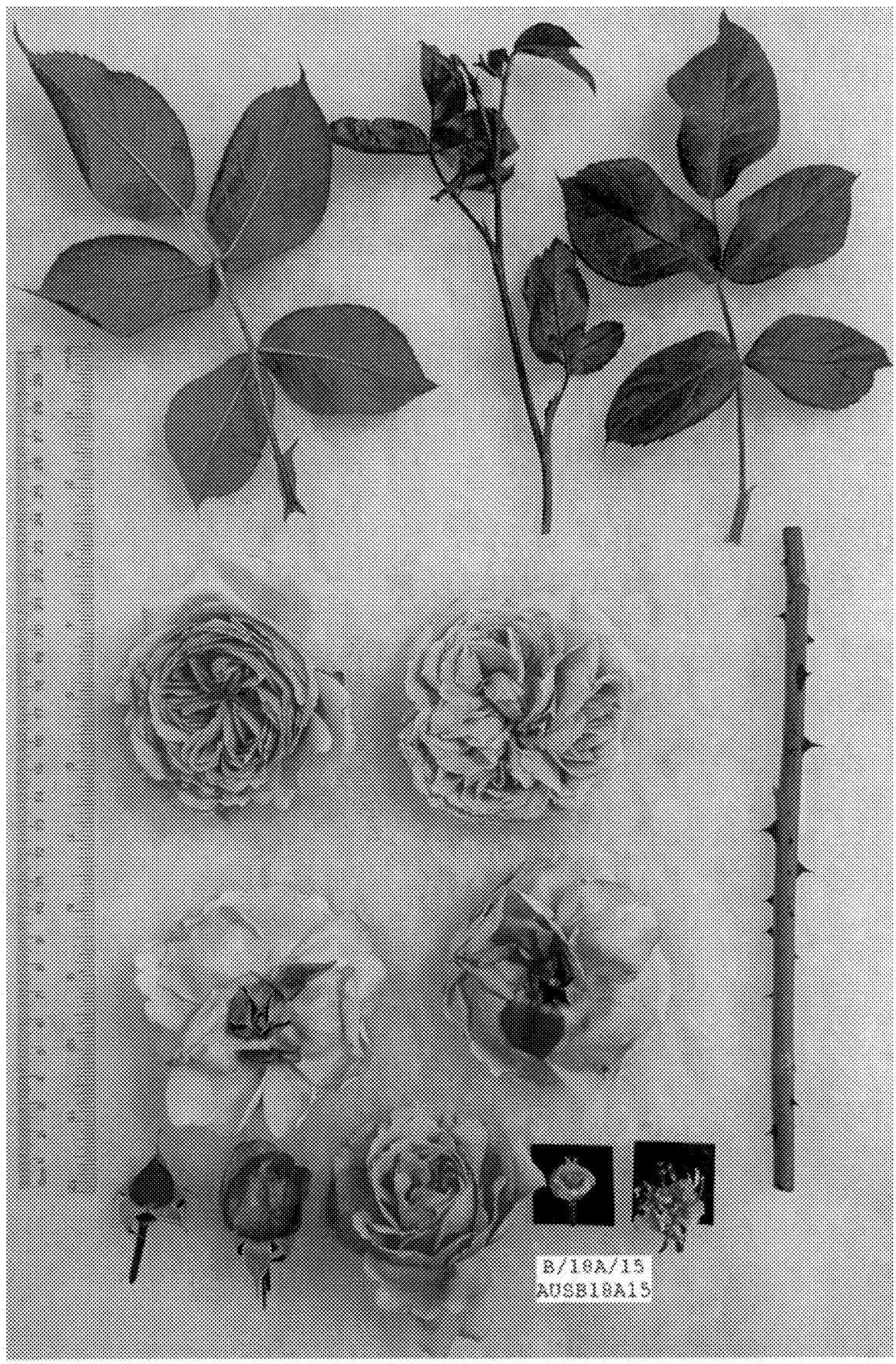
B/18A/15
AUSB18A15